United States Patent
Anderson et al.

[19]

[11] Patent Number: 6,074,341
[45] Date of Patent: Jun. 13, 2000

[54] VESSEL OCCLUSIVE APPARATUS AND METHOD

[75] Inventors: David W. Anderson, Maple Grove; Gerald W. Timm, Minneapolis, both of Minn.

[73] Assignee: Timm Medical Technologies, Inc., Eden Prairie, Minn.

[21] Appl. No.: 09/094,055

[22] Filed: Jun. 9, 1998

[51] Int. Cl.$^7$ .......................................... A61F 2/00

[52] U.S. Cl. ...................................... 600/29; 128/DIG. 25

[58] Field of Search .................................. 600/29–30, 38, 600/41, 490, 499; 128/DIG. 25; 606/151–158, 201

[56] References Cited

U.S. PATENT DOCUMENTS

| | | |
|---|---|---|
| 3,744,063 | 7/1973 | McWhorter et al. |
| 3,810,259 | 5/1974 | Summers . |
| 3,863,622 | 2/1975 | Buuck . |
| 4,118,805 | 10/1978 | Reimels . |
| 4,417,567 | 11/1983 | Trick . |
| 4,474,187 | 10/1984 | Timm et al. |
| 4,515,166 | 5/1985 | Timm . |
| 4,571,749 | 2/1986 | Fischell . |
| 4,584,990 | 4/1986 | Haber et al. |
| 4,606,353 | 8/1986 | Timm . |
| 4,731,083 | 3/1988 | Fischell . |
| 4,766,909 | 8/1988 | Timm et al. |
| 4,784,660 | 11/1988 | Fischell . |
| 4,829,990 | 5/1989 | Thuroff et al. |
| 4,848,631 | 7/1989 | Penney et al. |
| 4,911,176 | 3/1990 | Timm et al. |
| 4,958,630 | 9/1990 | Rosenbluth et al. |
| 5,184,629 | 2/1993 | Erickson et al. |
| 5,704,893 | 1/1998 | Timm . |

FOREIGN PATENT DOCUMENTS

WO 84/01098  3/1984  WIPO .

OTHER PUBLICATIONS

Exhibit A: Product Information Brochure, *Snap–Gauge* ® *Impotence Screening Device*, by Dacomed Corporation, 1 pg. (1988) (Form No. 710–036–1089).
Exhibit B: Brochure, *Don't Think of it as Simply an Addition to Your Practice, Think of it as Multiplication*, by Dacomed Corporation, 1 pg. (1989).
Exhibit C: Product Information Brochure, *Rigiscan Ambulatory Rigidity & Tumescence Monitor*, by Dacomed Corporation, 1 pg. (1989(Form No. 750–197–0389).
Exhibit D: Product Information Brochure, *Rigiscan* ® *DT Monitor*, by Dacomed Corporation, 1 pg. (1988) (Form No. 750–261–1089).
Exhibit E: Brochure, *Finally, A Way to Control Male Incontinence Without All The Risk*, by Dacomed Corporation, 1 pg. (1989).
Exhibit F: Product Information Brochure, *C$^3$® Male Continence Device*, by Dacomed Corporation, 1 pg. (1989) (Form No. 910–279–0194).
Exhibit G: Abstract of Societe Internationale D'Urologie, 23rd Congress, Sep. 18–22, 1994, Sydney, Australia.
Exhibit H: Abstract of American Urological Association, "IC#13 Artificial Urinary Sphincters," May 15, 1994, San Francisco, California.

(List continued on next page.)

*Primary Examiner*—John P. Lacyk
*Attorney, Agent, or Firm*—Merchant & Gould P.C.

[57] ABSTRACT

An occlusive apparatus and method for reversibly occluding fluid conveying vessels in the body. In one embodiment, the occlusive apparatus includes an occlusive member adapted for at least partially encircling a vessel, with the occlusive member including an intrinsic spring force therein for exerting an occluding pressure on the vessel while the occlusive member at least partially encircles the vessel. A control mechanism is operatively connected to the occlusive member, with the control mechanism being arranged and configured to counteract the intrinsic spring force of the occlusive member and thereby remove the occluding pressure on the vessel while the occlusive member is at least partially encircling the vessel.

34 Claims, 5 Drawing Sheets

OTHER PUBLICATIONS

Exhibit I: *Urologic Clinics of North America*, vol. 16, No. 1, Feb., 1989, pp. 99–117.

Exhibit J: *IEEE Transactions on Bio–Medical Engineering*, vol. BME–17, No. 4, Oct., 1970, pp. 352.

Exhibit K: *J. Biomechanics*, vol. 4, pp. 213–219, 1971.

VESSEL OCCLUSIVE APPARATUS AND METHOD

FIELD OF THE INVENTION

The present invention relates to an apparatus and method for occluding fluid conveying vessels in the body. In particular, the present invention relates to an apparatus and method to replace the absent or damaged sphincteric function of a variety of bodily organs. The present invention has particular use for occluding the urethra so as to restore urinary continence to patients with urinary control problems. Other areas of application of the present invention include, but are not limited to, the gastroesophageal sphincter and rectal sphincter in both men, women and children.

BACKGROUND OF THE INVENTION

Urinary incontinence is a frequent and distressing sequel to various neurological diseases, surgical procedures, spinal cord injury, etc. Various urethral occlusive devices have been developed in an effort to restore urinary continence to patients with urinary control problems.

In particular, devices utilizing hydraulic sphincters or cuffs have been used to provide urethral occlusion. See for example:

Timm, G. W.; Merrill, D. E. and Bradley, W. E. "Intermittent Occlusion System"; IEEE Transactions On Bio-Medical Engineering; BME-17:352; 1970;

Timm, G. W., "An Implantable Incontinence Device"; J. Biomechanics; 4:213–219; 1971; and U.S. Pat. Nos. 3,744,063; 3,863,622; 4,571,749; 4,731,083; and 4,784,660.

One particular problem with hydraulic sphincters or cuffs is that they often do not apply uniform pressure on the urethra. As the cuff or sphincter is inflated, it folds or changes its shape, often in a non-uniform manner, thereby exerting uneven occlusion force on the urethra. This can result in urethral erosion or urethra tissue being worn away after extensive use.

Another approach to treating urinary incontinence is to surgically adjust the angle between the urethra and the bladder. This angle is often referred to as the angle of the urethro vesical junction. Of course, a problem with this procedure is that the effects of the surgery cannot be readily changed and requires trained medical professionals to do so.

The present invention offers a substantial improvement over existing vessel occlusive apparatus and methods.

SUMMARY OF THE INVENTION

The present invention relates to an occlusive apparatus and method for reversibly occluding fluid conveying vessels in the body.

The present invention has numerous applications for controlling and/or occluding fluid flow in the fluid conveying vessels in humans and/or animals. Its applications include control of fecal incontinence, venous outflow from a penis thereby controlling impotence, bile duct flow, male and female fertility, blood flow in blood vessels, etc. The present invention can be used in conjunction with most any vessel in the body. In many applications, the present invention will occlude the vessel as required to stop or prohibit fluid flow. In other applications, the present invention will control the amount of fluid flow through the vessel.

In one embodiment in accordance with the present invention, an occlusive apparatus for reversibly occluding a fluid conveying vessel is provided. The occlusive apparatus includes an occlusive member adapted for at least partially encircling the vessel, with the occlusive member including an intrinsic spring force therein for exerting an occluding pressure on the vessel while the occlusive member at least partially encircles the vessel. A control mechanism is operatively connected to the occlusive member, with the control mechanism being arranged and configured to counteract the intrinsic spring force of the occlusive member and thereby remove the occluding pressure on the vessel while the occlusive member is at least partially encircling the vessel.

In another embodiment in accordance with the present invention, an apparatus for reversibly occluding a fluid conveying vessel is provided. The apparatus includes an occlusive member adapted for at least partially encircling the vessel, with the occlusive member including an intrinsic resilient biasing force which biases the occlusive member to a contracted state for exerting an occluding pressure on the vessel while the occlusive member at least partially encircles the vessel. A control mechanism is operatively connected to the occlusive member for actuating the occlusive member to an expanded state. The control mechanism is arranged and configured to counteract the intrinsic resilient biasing force of the occlusive member and thereby force the occlusive member to the expanded state and remove the occluding pressure on the vessel while the occlusive member is at least partially encircling the vessel.

In a preferred embodiment, the occlusive member is in the form of a loop or ring, which exerts a predetermined, radial pressure evenly about the vessel sufficient to prevent fluid flow through the vessel. The radial pressure is removed by the control mechanism to allow unobstructed flow through the vessel.

In yet another embodiment, the occlusive member is in the form of a sling which underlies the vessel for occluding flow through the vessel. The control mechanism is utilized to lower the sling, thereby allowing unobstructed flow through the vessel.

In yet another embodiment in accordance with the present invention, an expandable and contractable member is adapted for at least partially encircling a body vessel, with the member including an intrinsic resilient biasing force which biases the member to a contracted state. An abdominal pressure sensor adapted for sensing abdominal pressure is provided for providing inputs to a control mechanism that is operatively connected to said member. The control mechanism is arranged and configured to control expansion and contraction of the member in response to the abdominal pressure sensed by the abdominal pressure sensor.

In still another embodiment in accordance with the present invention, a method for controlling fluid flow in a fluid conveying vessel is provided. The method includes the steps of surrounding at least a portion of the vessel with a member that is resiliently biased to a contracted state such that an occluding pressure is exerted on the vessel when the member is in the contracted state, and selectively forcing the member to an expanded state thereby at least partially removing the occluding pressure on the vessel.

An advantage off the invention is that the apparatus is totally implantable in the body of the patient. Another advantage is that the implantable apparatus requires no tubes, wires or other external control mechanism passing through the skin of the patient.

A further advantage of the present invention is that the occlusive apparatus has a unitary construction and may be implanted into the patient through a single surgical incision.

Previous occlusive devices have frequently required two surgical incisions with the larger attendant risk of infection, incomplete healing and longer convalescence times.

Another advantage of the present invention is that the occlusive member is capable of large changes in diameter, and as such will accommodate a larger range of vessel diameters and changes in vessel diameters. Previous occlusive devices offer many different sizes and pressure options requiring many different components for the surgeon to choose from and stock in the hospital, thereby increasing the complexity of using these previous devices and increasing costs.

Since the occlusive apparatus of the present invention is of unitary construction, it does not require intra-operative connection of components. Previous occlusive devices have required multiple components to be connected together by the surgeon, which increase the intra-operative time and fatigue, with a risk of component disconnection after implantation.

Further, the occlusive apparatus of the present invention does not have to be filled with liquid as previous devices have required. This saves on intra-operative time and the potential for fluid leakage in the event of a disconnection or device fatigue is eliminated.

The occlusive member of the present invention is also narrower than current devices utilizing hydraulic cuffs. It is believed that this reduction in width reduces the amount of tissue dissection to implant the member, while achieving the same occlusive pressure as the larger width devices, thereby reducing the tendency for the vessel to atrophy or erode.

Further, previous hydraulic urethral cuffs have tended to form folds and pillows when encircling the urethra. The occlusive member in one embodiment of the present invention encircles the urethra in a circular fashion and applies pressure to the urethra evenly over its entire circumference. This reduces the risk of urethral erosion and increases the occlusive efficiency.

These and various other features and advantages of novelty which characterize the invention are pointed out with particularity in the claims annexed hereto and forming a part hereof. However, for a better understanding of the invention, its advantages and objects obtained by its use, reference should be had to the drawings which form a further part hereof, and to the accompanying descriptive matter, in which there is illustrated and described the preferred embodiment(s) of the invention.

BRIEF DESCRIPTION OF THE DRAWINGS

In the drawings in which like reference numerals and letters generally indicate corresponding parts throughout the several views.

DETAILED DESCRIPTION OF THE PREFERRED EMBODIMENT

As noted above, the apparatus and method of the present invention might be utilized in conjunction with any number of different vessels in humans and animals which are used to convey fluid. The following are some examples of various applications of the present invention, however this list is by no means exhaustive of the numerous applications in which the present invention may be used. The occluding apparatus of the present invention might be used to control fecal incontinence or bowel movements, to control venous outflow from a penis and thus control impotence, to control bile duct flow, to control fluid flow in the vas deferens and thus male fertility, to control fluid flow in the fallopian tubes and thus control female fertility, to control blood flow in blood vessels for vascular studies or the like, etc.

The above noted examples are but a few of the many applications of the present invention. The invention will now be described more particularly in view of its application for occluding the urethra and thus controlling incontinence. It will be appreciated that the urethra is shown with only a single lumen or passageway. However, in many applications, such as controlling venous outflow from the penis, there are multiple lumens which will be occluded by the present invention.

A urethral occlusive apparatus in accordance with the present invention in the preferred embodiment is designed to be totally implantable into a body. The apparatus has no tubes or wires or other electromechanical connection passing through the skin. Additionally, in the preferred embodiment, no external appliances are required to operate the occlusive apparatus. However, coupled coils might be used either for continuous powering of the device or to recharge batteries which are implanted to power the apparatus, when the apparatus is automated.

In a preferred embodiment, the occlusive apparatus of the present invention has a unitary construction and may be implanted into the patient through a single surgical incision. Further, the occlusive apparatus of the present invention is of unitary construction, and does not require intra-operative connection of components. The occlusive apparatus of the present invention is also designed to accommodate a larger range of vessel diameters and changes in vessel diameters.

In the preferred embodiment, the urethral occlusive apparatus is made of materials, as well as having a geometric configuration, which is compatible with the body. Suitable materials used might include implantable grade polymeric materials, titanium and titanium alloys, and stainless steels. Preferably, all surfaces in contact with body fluids and/or tissues meet the required, e.g. class 6 U.S.P., tests for toxicity and pyrogenicity. In addition, corners and edges are rounded and surfaces are nonabrasive to body structures. The urethral apparatus of the present invention is also lightweight so as to minimize any chance for migration.

In the preferred embodiment, the operation of the urethral occlusive apparatus is easily understood and readily controlled by the user requiring a minimal amount of manual or mental dexterity. Operation of the apparatus is accomplished through intact skin. The control mechanism of the urethral apparatus shall be of a size to be readily grasped by the user. In an alternative embodiment, the control mechanism may be electro-mechanically controllable or controlled by other wireless means such as batteries, coupled coils or radio frequency (RF) signals.

In the preferred embodiment, the occlusive force exerted against the urethra shall be sufficient to prevent urinary leakage, but not so great that the urethral viability is impaired. Preferably, the pressure shall not exceed 100 cm $H_2O$ for more than 10 minutes when in the activated state. Moreover, the urethral occluding apparatus shall not interfere with urine flow when in the expanded or deactivated state.

Alternate embodiments of the urethral occluding apparatus shall have automatic occluding pressure release capabilities with high intra-vesical pressure. In one preferred embodiment, a detrusor muscle contraction (bladder muscle contraction) producing an intra-vesical pressure greater than 120 cm $H_2O$ (estimated normal voiding pressure) shall result in release of pressure against the urethra upon being sensed by an abdominal sensor present in the urethral occluding apparatus.

Preferably, a non-functioning urethral occluding apparatus of the present invention shall leave the patient in his/her preimplant incontinent condition. The device shall be inert to the presence of body tissues, and materials forming the occluding apparatus shall be of an implantable quality and be non-allergenic to the patient. Preferably, the occluding apparatus will prevent leakage during coughing, straining or other sudden increases in abdominal pressure. A preferred embodiment of the occluding apparatus shall contain a sensor to be placed in the abdominal cavity to feed back pressure information to a controller. The sensor senses intra-abdominal, extravesical pressure that causes intra-vesical pressure (i.e. bladder pressure) to rise without a detrusor muscle contraction. When this occurs in the presence of impaired urinary sphincter contractibility, urinary incontinence occurs. A sensor could also be provided to sense neural impulses related to detrusor muscle activity and cause the urethral occluding apparatus to respond appropriately.

Preferably materials used in the system shall not deteriorate in contact with body fluids and tissue so as to provide the occluding apparatus with long-term usage. In the preferred embodiment, the maximum obtainable pressure in the activated condition of the occluding apparatus shall be inherent and therefore not dependent upon the ability of the user to manipulate the apparatus.

Figure 1:
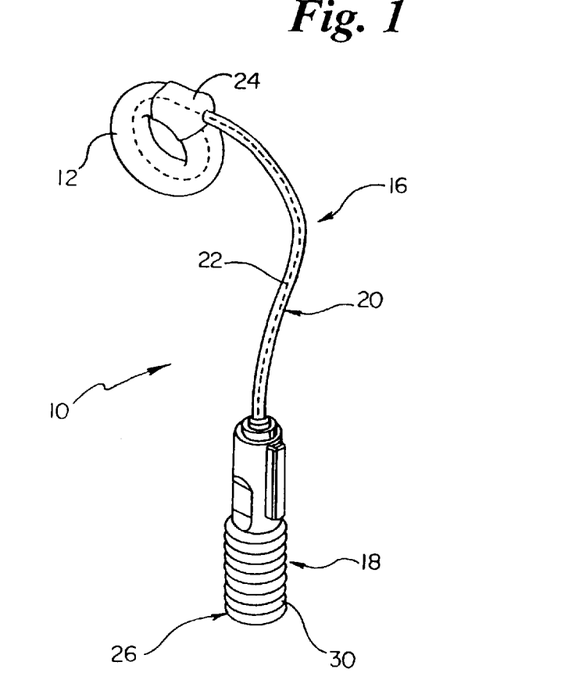
FIG. 1 is a perspective view of an occlusive apparatus in accordance with the principles of the present invention.
Figure 2A:
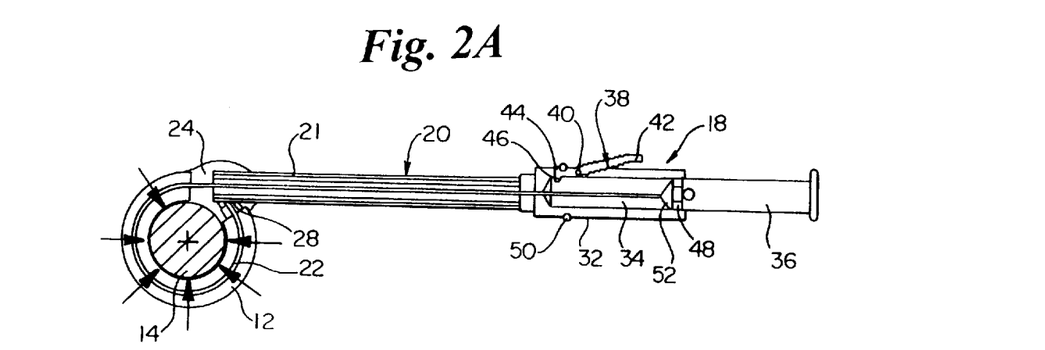
FIGS. 2A and 2B are side elevational views of the occlusive apparatus shown in FIG. 1, in an activated condition and a deactivated condition, respectively.
Figure 2B:
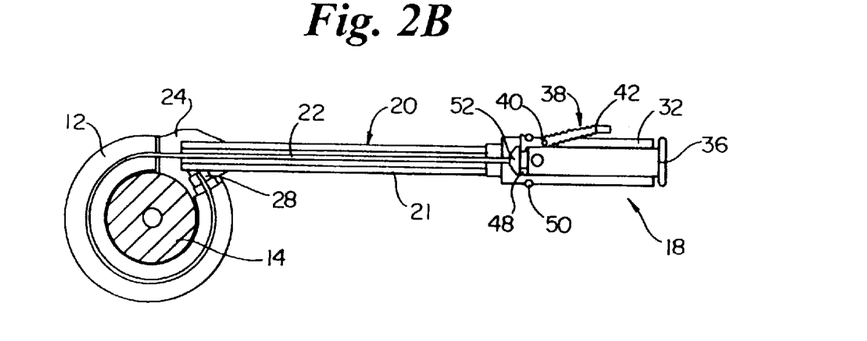
Figure 3:
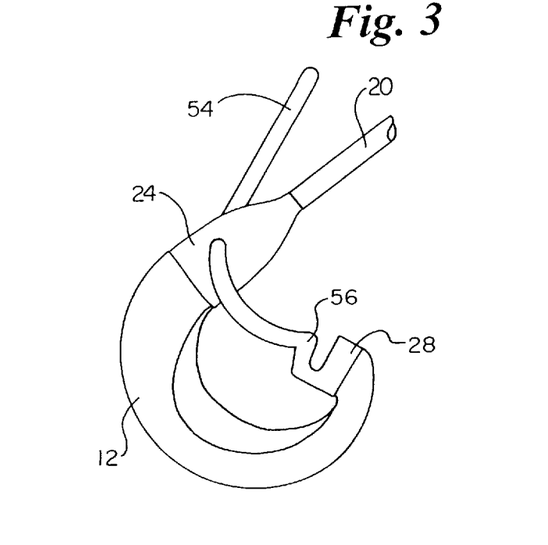
FIG. 3 is a diagrammatic view of the occlusive member which forms a portion of the occlusive apparatus, which illustrates how the ends of the occlusive member are connected together.

More particularly, there is illustrated in FIGS. 1–3 a preferred embodiment of the occluding apparatus of the present invention, generally referred to by the reference numeral 10. The occluding apparatus 10 includes an occlusive member 12 in the form of a loop that is movable between a contracted, activated condition as shown in FIG. 2A and an expanded, de-activated condition as shown in FIG. 2B. The occlusive member 12 encircles the urethra 14 in males (or the bladder neck in females and young males) and exerts a predetermined, radial occluding pressure evenly about the urethral or bladder neck circumference when in the contracted condition. This occluding pressure is sufficient to prevent urine leakage during events where the bladder pressure is increased, for instance due to coughs, sneezes, sporting activities, etc. When the occlusive member 12 is moved to the expanded, de-activated condition, unobstructed urinary drainage is allowed.

The occlusive member 12 is constructed to have an intrinsic radial spring or biasing force therein which radially biases the occlusive member 12 to the contracted condition. Thus, the occlusive member 12 is normally biased to the contracted condition, shown in FIG. 2A, and exerts an occluding pressure on the urethra 14 to prevent urine flow. To permit urine flow, the biasing force in the occlusive member 12 must be removed or counteracted by forcing the occlusive member 12 to the expanded or stretched condition shown in FIG. 2B.

In the preferred embodiment, the occlusive member 12 is constructed from an expandable and compressible material, such as expanded polytetraflouroethylene (ePTFE), which in its compressed state, is coated with an elastomeric material, such as silicon rubber. Therefore, any expansion or stretching of the ePTFE substrate will cause the elastomeric silicone rubber coating to stretch in a manner equivalent to that of a constant force spring. It is this force that forms the intrinsic biasing force of the occlusive member 12, thereby biasing the occlusive member to the contracted condition and imparting the occlusive pressure to the urethra.

The occlusive member 12 is designed to accommodate a wide range of urethra and bladder neck sizes, such as urethras with circumferences ranging from about 3.5 cm. to about 6.0 cm., or bladder necks with circumferences ranging from about 6.0 cm. to about 12.0 cm., and the occlusive member 12 has a reduced width, such as a width of approximately 1.0 cm.

The occlusive pressure of the occlusive member 12 may be manually removed by the patient, i.e. the occlusive member 12 is forced to the expanded condition of FIG. 2B, to allow unobstructed urinary flow. To remove the occluding pressure, the occluding apparatus 10 includes a control mechanism 16 which is joined to the occlusive member 12 for counteracting the biasing force of the occlusive member to force the occlusive member to the expanded condition. The control mechanism 16 includes an actuator 18, a conduit tube 20 joining the occlusive member 12 and the actuator 18, and an elongate wire member 22 that is connected at one end to the actuator 18 and extends through the conduit tube 20 and the occlusive member 12 where the wire 22 is fixed at its opposite end. The actuator 18, which is implanted in the scrotum of a male or the labia of a female, is manually manipulated by the patient, to apply a pushing force to the wire 22 so as to advance the wire through the conduit tube 20. Since one end of the wire 22 is fixed in the occlusive member 12, advancement of the wire by the actuator 18 causes the occlusive member to expand or stretch, thereby removing the occluding pressure. Upon release of the actuator 18, the biasing force of the occlusive member forces the wire 22 back, so that the occlusive member 12 returns to its contracted condition.

The conduit tube 20 is extruded from a polymeric material, such as ePTFE similar that used for the occlusive member 12, and is connected at one end thereof to the occlusive member 12 by a shroud 24 and connected at its opposite end to a flexible, silicon rubber boot 26 encasing the actuator 18. The ePTFE material of the tube 20, in its fully stretched state, is coated with silicon rubber 21. Thus, the ePTFE material is not free to stretch in this condition and therefore does not act like a spring. The silicon rubber layer 21 of the conduit tube 20 is intended to prevent tissue ingrowth that may occur during tissue healing after surgery to implant the occluding apparatus 10, to facilitate adhesive bonding between the shroud 24 and the boot 26, improve kink resistance of the tube 20, and to prevent influx of bodily fluids into the inner cavities of the apparatus 10. The ePTFE material of the conduit tube 20 also provides a low friction surface over which the wire 22 can travel, as well as minimizing stretching of the tube 20.

The conduit tube 20 is suitably dimensioned for disposition within the body. Preferably, the conduit tube measures about 6 to about 10 inches in length, and has an outside diameter of about 0.15 inches. Other tube dimensions could be used however, depending upon the size of the patient the apparatus 10 is to be used in.

The wire 22 is connected at one end to the actuator 18, extends through the conduit tube 20 and through the occlusive member 12, and is attached at its second end to a clip 28 that forms a portion of the occlusive member 12. It is the wire 22 that transmits force to the occlusive member 12, when actuated by the actuator 18, so as to counteract the intrinsic biasing force of the occlusive member and force the occlusive member to the expanded condition. As the wire 22 is advanced by the actuator 18, the wire loop within the occlusive member 12 increases in diameter thereby forcing the occlusive member 12 to increase in diameter as well, so as to remove the occluding pressure from the urethra 14. Maintenance of this increased diameter condition of the occlusive member allows unobstructed voiding by the patient and allows removal of the occlusive force during a post-surgical healing period.

The wire 22 is manufactured from a suitable implant grade material having elastic properties to minimize permanent kinking of the wire which may occur when the conduit tube 20 is flexed during implantation or when the conduit tube 20 and occlusive member 12 are flexed by forces applied during normal activity of the patient. One suitable material for the wire is a nickel titanium alloy having superelastic properties. Other materials could be used as well.

As mentioned earlier, the actuator 18, which is encased within the flexible silicon rubber boot 26, is implanted in the scrotum of a male or the labia of a female, and allows the patient to manually actuate the occlusive member 12 to the expanded condition. The actuator 18 can measure about 5.0 cm×1.2 cm×1.0 cm to allow implantation, however other actuator sizes can be used as well, as long as the actuator can be implanted into the intended area. The rubber boot 26, as illustrated in FIG. 1, is disposed around the actuator 18 and is intended to allow actuation of the actuator while preventing tissue ingrowth and ingress of bodily fluids into the actuator. As will become evident below, the boot 26 includes a bellows portion 30 which facilitates actuation of the actuator 18.

With reference to FIGS. 2A and 2B, in which the boot 26 is removed to illustrate the details of the actuator 18, it is seen that the actuator 18 includes an actuator housing 32 to which one end of the conduit tube 20 is attached. The housing 32 includes a central bore 34 in which is slideably received a plunger 36, with one end of the wire 22 being suitably fastened to the plunger 36. The plunger 36 is freely slideable within the bore 34 of the housing 32 between an activated position shown in FIG. 2A and a deactivated position shown in FIG. 2B. In the activated position of FIG. 2A, the wire 22 and plunger 36 are forced by the intrinsic biasing force of the occlusive member 12 to the activated position so that the plunger 36 extends substantially past the end of the housing 32 ready to be actuated by the patient. When the plunger 36 is depressed by the patient to the deactivated position of FIG. 2B, the wire 22 is advanced to force the occlusive member 12 to the expanded condition, as described above, thereby deactivating the occlusive apparatus 10 and allowing the patient to void urine.

A locking mechanism is provided to lock the plunger 36 at the deactivated position, so as to allow unobstructed voiding by the patient and to remove the occlusive force of the occlusive member 12 during the post surgical healing period. The locking mechanism includes a lever 38 that is pivotally connected to the housing 32 by a pin 40, so that the lever 38 is able to pivot about the axis of the pin 40. One end 42 of the lever 38 extends outside of the housing 32 and the other end 44 of the lever extends through the housing and into the bore 34. The end 44 of the lever 38 includes an inwardly extending detent shoulder 46 thereon, and the end of the plunger 36 includes a circumferential detent groove 48 formed therein.

The lever 38 is biased in a counterclockwise direction about the axis of the pin 40 by a resilient o-ring 50 disposed around the housing 32 and the end 44 of the lever. The end of the plunger 36, forward of the detent groove 48, has a conic or frustoconic surface 52, which engages the detent shoulder 46 as the plunger 36 is moved to the deactivated position. The engagement between detent shoulder 46 and the surface 52 forces the lever 38 to pivot clockwise, against the bias of the o-ring 50, until the plunger 36 is moved to a position where the detent shoulder 46 drops into the detent groove 48 and is maintained therein by the bias of the o-ring 50. The plunger 36 is thus locked at the deactivated position, with the occlusive member 12 maintained at the expanded condition. To reapply occlusive pressure to the urethra 14, the patient locates the portion of the boot 26 overlying the lever 38 and simply presses the end 42 of the lever 38 downward, thereby lifting the detent shoulder 46 out of the detent groove 48, which allows the intrinsic biasing force of the occlusive member 12 to force the wire 22 and plunger 36 back to the activated position.

To facilitate depression of the plunger 36, the bellows portion 30 of the boot 26 is disposed over the plunger 36 so that the boot can easily deform when the plunger is being depressed. The housing 32, plunger 36 and lever 38 may be manufactured from an implant grade titanium material, such as wrought Titanium-6 Aluminum-4 Vanadium alloy, or a semi-rigid thermoplastic material, such as polysulfone.

In the preferred embodiment, the occlusive member 12 of the occlusive apparatus 10 is packaged and ready for implantation within the patient in a non-loop, open state. Thus, the occlusive member 12 is specifically designed to allow formation of the occlusive member 12 into a loop. With reference now to FIG. 3, it is seen that the clip 28 is disposed at one end of the occlusive member 12. The clip 28 includes a pull tab 54 attached thereto which allows a surgeon to pull the occlusive member through a pocket that has been dissected around the urethra or bladder neck.

To form the occlusive member 12 into a loop or ring, the pull tab 54 is inserted into a hole formed through the shroud 24 that joins the occlusive member 12 and the conduit tube 20, and the pull tab 54 is pulled through the shroud. As the pull tab 54 is pulled through the shroud, the occlusive member 12 begins to form a ring around the urethra. The clip 28, which is formed with a hook 56, eventually reaches the shroud 24, at which point the hook 56 extends into the hole in the shroud 24 and the area of the clip between the hook 56 and the rest of the clip 28 clips onto the shroud 24, thereby locking the occlusive member 12 into an encircling position around the urethra 14. The exposed end of the pull tab 54 is then trimmed away by the surgeon.

Figure 4A:
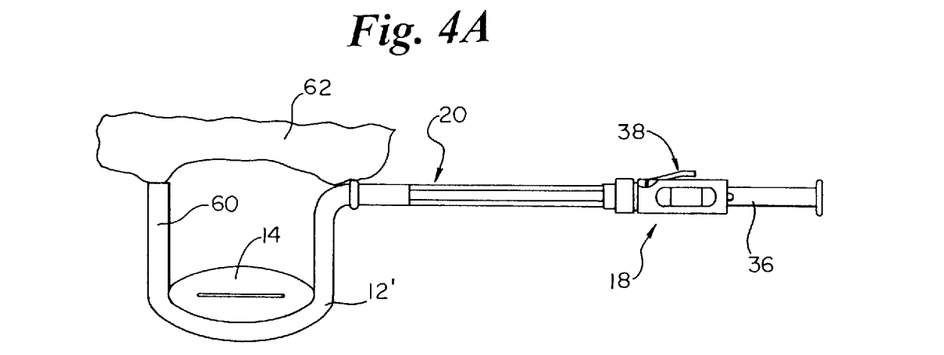
FIGS. 4A and 4B are diagrammatic views of another embodiment of the occlusive apparatus of the present invention in which the occlusive member forms a sling for the vessel, with FIG. 4A illustrating the activated condition and FIG. 4B illustrating the deactivated condition.
Figure 4B:
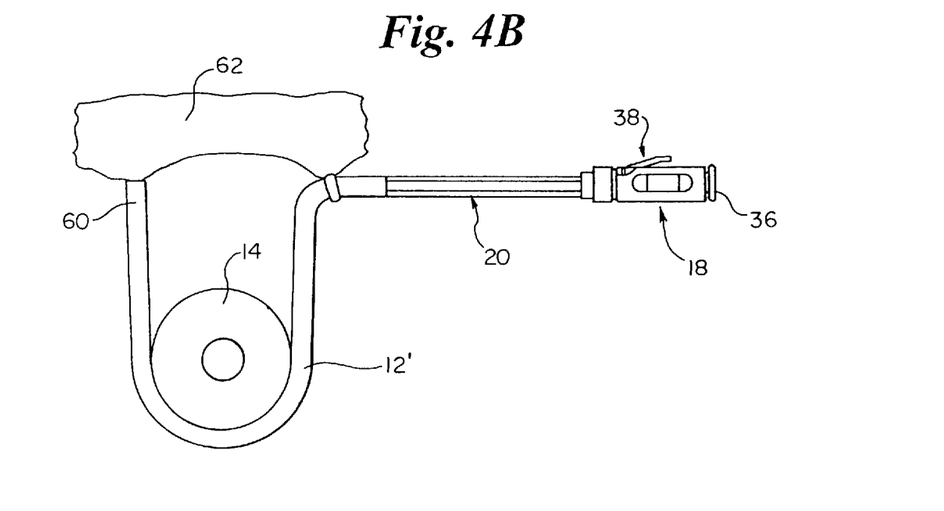
Figure 5A:
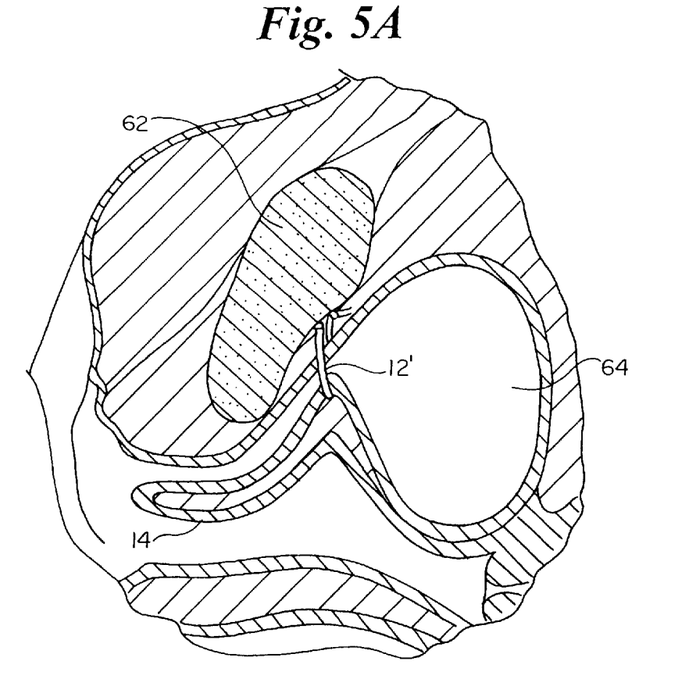
FIGS. 5A and 5B are diagrammatic views showing the embodiment of FIGS. 4A and 4B, respectively, interacting with a urethra.
Figure 5B:
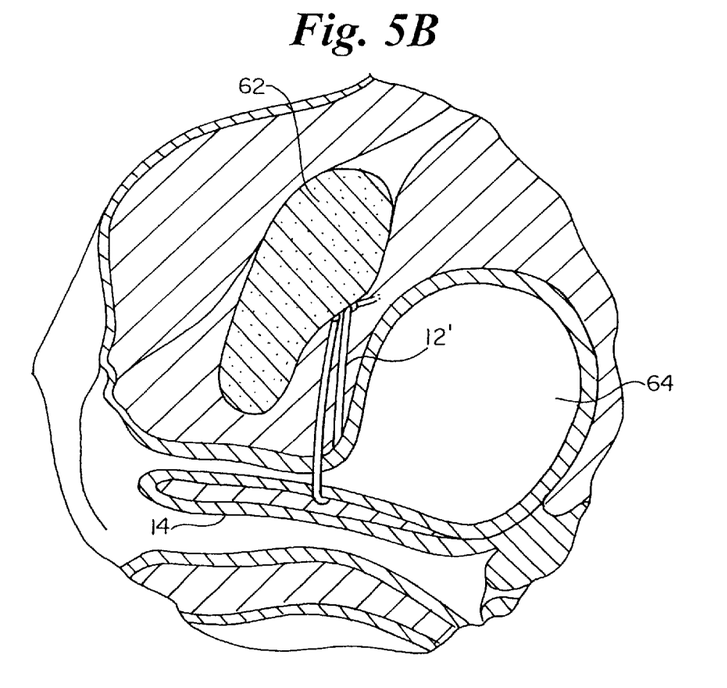

FIGS. 4A and 4B illustrate another embodiment of the invention wherein the occlusive member 12' is in the form of a U-shaped sling which underlies the urethra or bladder neck 14. One end 60 of the occlusive member 12' is attached to a pubic bone structure 62 in the patient on one side of the urethra 14. The occlusive member 12' extends underneath the urethra 14 and back upwards toward the bone structure 62, where the occlusive member 12' connects to the conduit tube 20, and where the occlusive member 12' and the conduit tube 20 are attached to the bone structure 62 on the other side of the urethra. Thus, in the activated position shown in FIG. 4A, the intrinsic biasing force of the occlusive member 12' causes the occlusive member 12' to be contracted, thereby reducing the overall length of the occlusive member 12' which elevates the sling so that the urethra is raised upward from its normal position. This can be seen in FIG. 5A which shows the urethra 14 and bladder 64, with the urethra elevated by the sling. Elevation of the urethra 14 bends or kinks the urethra, causing occlusion to occur. Upon actuation of the actuator 18, the occlusive member 12' is caused to expand or stretch to the deactivated position, shown in FIG. 4B. Expansion or stretching of the occlusive member 12' increases its length, thereby increasing the size of the "U" formed by the occlusive member 12', which lowers the urethra back to its normal anatomical position to allow unobstructed urinary flow. The lowered position of the urethra at the deactivated condition can also be seen in FIG. 5B.

Figure 6:
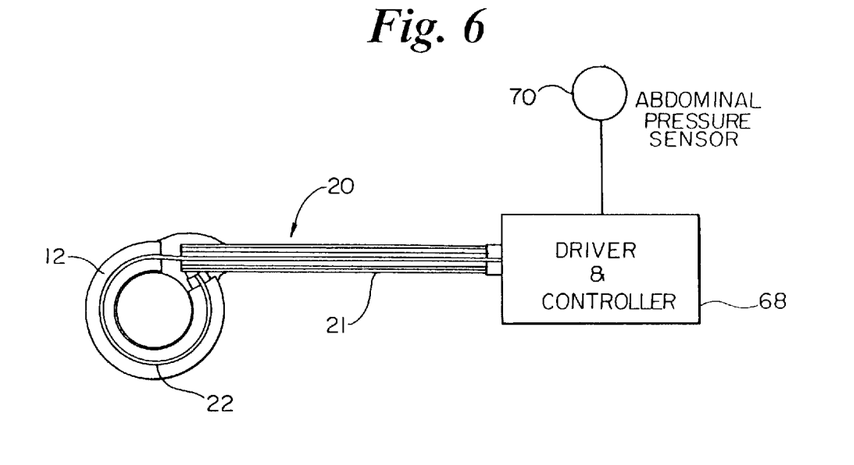
FIG. 6 is a diagrammatic view of still another embodiment of the occlusive apparatus in accordance with the present invention which is configured for automated operation.

FIG. 6 illustrates yet another embodiment of the invention, in which operation of the occlusive apparatus 10 is automatically controlled. The control mechanism 16 of this embodiment replaces the actuator 18 with a driver 68 that is operatively coupled to the wire member 22 for controlling operation of the apparatus 10. The driver 68, which can be an electric motor or other suitable electrically powered motor, preferably includes a power source, such as a battery or batteries, which supplies power to the driver. Alternatively, the driver 68 could be connected to externally supplied power outside the patient. The driver 68 preferably includes a driver controller that is integral therewith for controlling the operation of the driver. An abdominal pressure sensor 70 is electrically connected to the driver 68 for providing inputs to the driver controller of the driver.

The pressure sensor 70 is preferably placed in the prevesical space next to the urinary bladder to sense intra-abdominal pressure and send signals representative of the sensed pressure to the driver controller of the driver 68. Upon detection of a predetermined pressure by the pressure sensor 70, the occluding apparatus 10 is activated by the driver 68 according to a predetermined algorithm or pre-programmed logic within the driver controller. The algorithm provides for the apparatus 10 to be forced to the de-activated, non-occluding position when the sensed pressure is less than resting bladder pressure of approximately 20 cm $H_2O$. When intra-abdominal pressure exceeds 20 cm $H_2O$, the apparatus 10 is returned to the activated, occluding position to prevent urinary leakage. Thus, the occlusive member 12 is in its expanded state most of the time in which an occluding force is not being applied to the urethra, thereby reducing the risk of urethral erosion.

The driver controller might include interface capability for interconnection to various peripherals, including an adapter/charger which might be plugged into an AC outlet by a suitable power cord for powering the driver 68 or recharging the driver battery. The interconnection might be accomplished by coupled transformer coils or other suitable methods. The interconnection might also provide for external resetting and/or modification of the predetermined algorithm. Use of interconnection methods such as coupled transformer coils will allow the interface to be accomplished preferably without the use of wires or other physical connectors extending through the skin. It will be appreciated that this embodiment will preferably include program logic which can be readily programmed for different parameter settings, functions, etc. both before implantation of the occlusive apparatus 10 or after implantation.

Figure 7:
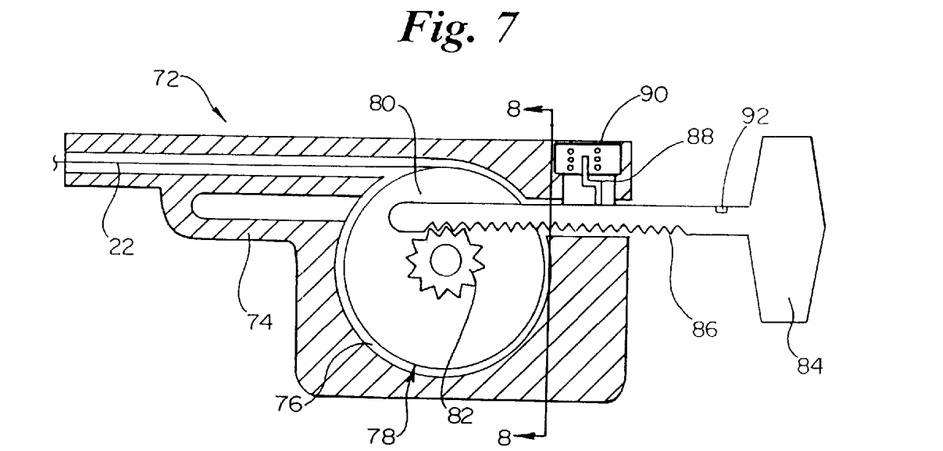
FIG. 7 is a side view of an alternate actuator for the occlusive member which provides a mechanical advantage.
Figure 8:
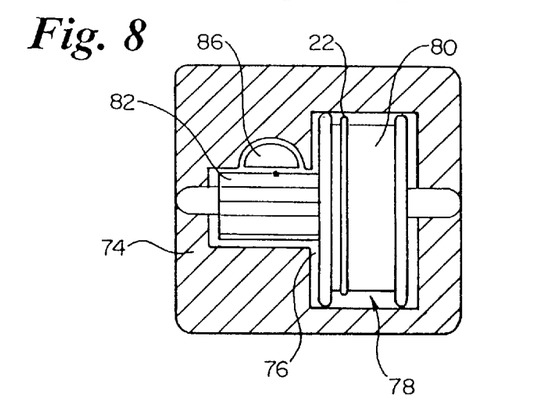
FIG. 8 is a cross-sectional view taken along line 8—8 of FIG. 7.

FIGS. 7 and 8 show an alternate embodiment of an actuator 72 that can be used to apply a pushing force to the wire member 22, thereby counteracting the biasing force of the occlusive member 12 to force the occlusive member to the expanded condition. In this embodiment, the actuator 72 includes a housing 74 having a central chamber 76 in which is rotatably mounted a mechanical advantage mechanism 78. The mechanical advantage mechanism 78 includes a spool 80 which is connected to the end of the wire member 22, and a pinion member 82 rigidly connected to the spool 80 and rotatable therewith. A plunger 84 having a rack 86 formed thereon slideably extends through the rear of the housing 74, with the rack 86 being in engagement with the pinion 82. As the plunger 84 is depressed, the rack 86 moves forward and drives the pinion 82 and the spool 80 counterclockwise. This advances the wire 22 forward, thereby forcing the occlusive member 12 to the expanded condition.

The diameter of the spool 80 is larger than the diameter of the pinion 82 in order to amplify the movement of the plunger 84, such that the distance that the patient must depress the plunger 84 to deactivate the occlusive member 12 is reduced. For instance, the spool could have a diameter of about 0.375 inches while the diameter of the pinion could have a diameter of about 0.188 inches, such that if the plunger 84 is depressed a distance of about 1.5 cm, the wire 22 is advanced a distance of about 3.0 cm. Of course, the spool and pinion could have other diameters as well, as long as the movement of the plunger is amplified.

The plunger 84 is also provided with a locking mechanism for locking the plunger at the deactivated position. The locking mechanism includes a stylus 88 which is biased into engagement with the plunger 84 on the side of the plunger opposite the rack 86 by a biasing spring 90. A stylus detent 92 is provided at the end of the plunger 84 which engages with the stylus 88 to lock the plunger at the deactivated position. The locking mechanism is constructed such that as the plunger 84 moves to the end of its depression stroke, the stylus 88 and detent 92 lock the plunger in the deactivated state. Depressing the plunger 84 again releases the stylus 88 from the detent 92, allowing the intrinsic biasing force of the occlusive member 12 to force the plunger back to its original activated state. Further details of such a locking mechanism and its operation can be found in U.S. Pat. No. 4,541,420, which disclosure is hereby incorporated by reference in its entirety.

Figure 9:
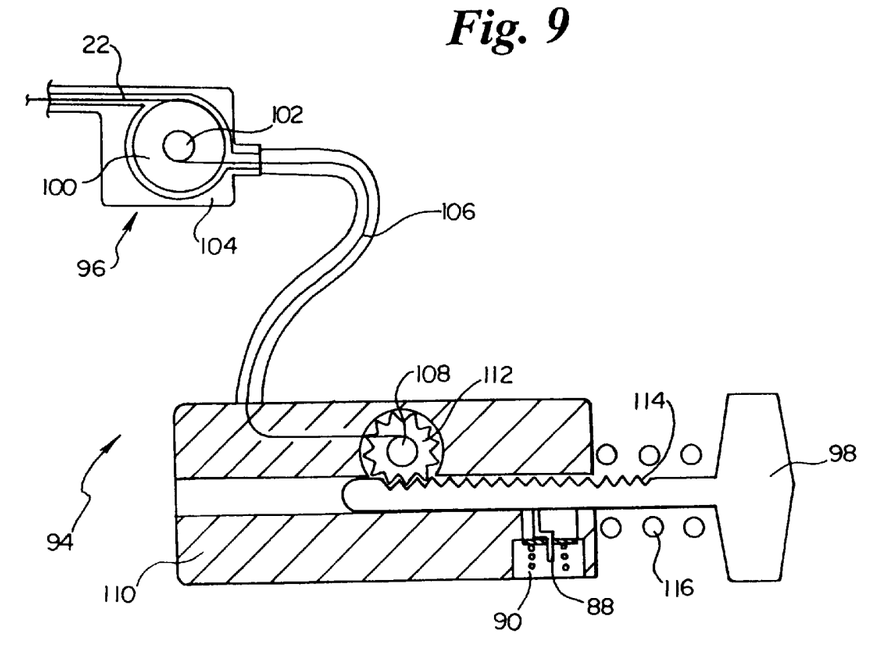
FIG. 9 is a side view of yet another alternate embodiment of an actuator.

A further actuator 94 is illustrated in FIG. 9, which is designed to reduce the size of the portion that is implanted within the scrotum or labia, as well as allowing a greater displacement magnification of the plunger. This embodiment includes a mechanical advantage mechanism 96 that is separate from a plunger 98. The mechanical advantage mechanism 96 includes a first, larger diameter spool 100 that is connected to the end of the wire 22 and a second, smaller diameter spool 102 that is rigidly connected to the first spool 100. The spools 100, 102 are rotatably mounted within a housing 104. A cable 106 is connected at one end thereof to the spool 102, and is connected at its opposite end to a spool 108 that is rotatably mounted within a plunger housing 110. The spool 108 is connected to a pinion 112 which is driven by a rack 114 formed on the plunger 98. A spring 116 extending between the housing 110 and the plunger 98 biases the plunger to the activated position. A locking mechanism, including a stylus 88 and spring 90, similar to the locking mechanism of FIG. 7, is also provided for locking the plunger 98 at the deactivated position.

In the embodiment of FIG. 9, as the plunger 98 is depressed, the rack 114 drives the spool 109 and pinion 112 clockwise, thereby tensioning or retracting the cable 106. As the cable 106 retracts, it drives the spools 100, 102 counterclockwise thereby advancing the wire 22 to force the occlusive member 12 to the expanded condition. Upon release of the plunger 98, the intrinsic biasing force of the occlusive member 12 and the spring 116 contribute to force the components back to the activated condition.

Figure 10:
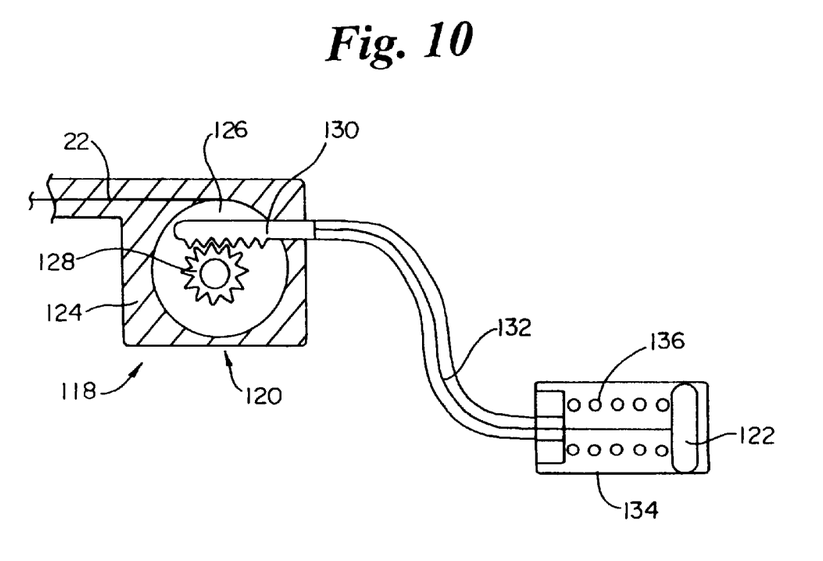
FIG. 10 is a side view of another embodiment of the actuator.

The actuator 118 of FIG. 10 is similar to the actuator of FIG. 9, including a separate mechanical advantage mechanism 120 and plunger 122. The mechanical advantage mechanism 120 includes a housing 124 in which are rotatably mounted a spool 126 connected to the wire member 22 and a pinion 128 connected to the spool 126 and rotatable therewith. A rack member 130 slidably extends through the housing 124 and engages with the pinion 128 for driving the spool 126 and pinion 128. A cable 132 is connected at one of its ends to the rack member 130 and connected at its opposite end to the plunger 122 which is slideably disposed within a plunger housing 134. A spring 136 disposed within the housing 134, biases the plunger 122 to the activated position.

In the embodiment of FIG. 10, as the plunger 122 is depressed, the cable 132 is advanced, thereby driving the rack member 130 forward which drives the spool 126 and pinion 128 in a counterclockwise direction. This counterclockwise rotation advances the wire 22 to force the occlusive member 12 to the expanded condition. Upon release of the plunger 122, the intrinsic biasing force of the occlusive member 12 and the spring 136 contribute to force the components back to the activated condition.

In each of the embodiments of FIGS. 7–10, the plunger, plunger housing and/or the mechanical advantage housing are preferably encased within a silicon rubber boot, similar to the boot 26. Further, the cables 106, 132 are preferably surrounded by a protective sheath similar to the tube 20, to allow sliding movements of the cables 106, 132 while preventing kinking of the cables, as well as preventing tissue ingrowth and ingress of bodily fluids.

Having read the foregoing description, it is to be understood that even though numerous characteristics and advantages of various embodiments in accordance with the principles of the invention have been set forth in the foregoing description, together with details of the structure and function of the invention, the disclosure is illustrative only, and changes may be made in detail, especially matters of shape, size and arrangement of the parts, within the principles of the invention to the full extent indicated by the broad general meaning of the terms in which the appended claims are expressed.

We claim:

1. An occlusive apparatus for reversibly occluding a fluid conveying vessel in a body, comprising:
    an occlusive member adapted for at least partially encircling the vessel, said occlusive member including an intrinsic spring force therein for exerting an occluding pressure on the vessel while the occlusive member at least partially encircles the vessel; and
    a control mechanism operatively connected to said occlusive member, said control mechanism being arranged and configured to counteract the intrinsic spring force of said occlusive member and thereby remove the occluding pressure on the vessel while the occlusive member is at least partially encircling the vessel.

2. The occlusive apparatus according to claim 1, wherein the occlusive member comprises an expandable and compressible polymeric material that is coated with an elastomeric material.

3. The occlusive apparatus according to claim 1, wherein the control mechanism comprises an elongate member having a distal end portion and a proximal end portion, said distal end portion extending through the occlusive member and being fastened thereto, and an actuator operatively connected to the proximal end portion for applying a pushing force to the proximal end portion to remove the occluding pressure.

4. The occlusive apparatus according to claim 3, wherein said elongate member comprises a wire.

5. The occlusive apparatus according to claim 4, wherein said wire includes an intermediate portion between said distal end portion and said proximal end portion, and further including a tube disposed around the intermediate portion, said intermediate portion being slideably disposed in said tube.

6. The occlusive apparatus according to claim 3, wherein said actuator comprises a plunger.

7. The occlusive apparatus according to claim 6, wherein said actuator further comprises a housing, and said plunger is connected to the housing and is slideable relative thereto.

8. The occlusive apparatus according to claim 7, wherein said plunger and said housing are encased within a flexible boot made of a biocompatible material.

9. The occlusive apparatus according to claim 7, wherein said plunger is slideable between an activated position and a deactivated position, and said actuator further includes a locking mechanism for locking the plunger at the deactivated position.

10. The occlusive apparatus according to claim 9, wherein said locking mechanism comprises a lever that is pivotally connected to the housing.

11. The occlusive apparatus according to claim 6, wherein said actuator further comprises a mechanical advantage mechanism interconnected between the elongate member and the plunger to amplify the movement of the plunger.

12. The occlusive apparatus according to claim 11, wherein said mechanical advantage mechanism includes a first spool operatively connected to the proximal end portion of said elongate member and a second member operatively connected to said plunger, said first spool having a diameter that is greater than a diameter of said second member.

13. The occlusive apparatus according to claim 12, wherein said second member comprises a spool.

14. The occlusive apparatus according to claim 12, wherein said second member comprises a pinion.

15. The occlusive apparatus according to claim 1, wherein said control mechanism includes an electro-mechanical driver operatively connected to the occlusive member for counteracting the intrinsic spring force therein, and an abdominal pressure sensor adapted for sensing abdominal pressure, the electro-mechanical driver being operable in response to the abdominal pressure sensed by the abdominal pressure sensor.

16. The occlusive apparatus according to claim 1, wherein the occlusive member is in the form of a loop for encircling the vessel.

17. The occlusive apparatus according to claim 16, wherein the occlusive member includes a first end portion and a second end portion, and means for connecting the second end portion to the first end portion so as to form the loop.

18. An apparatus for reversibly occluding a fluid conveying vessel in a body, comprising:

an occlusive member adapted for at least partially encircling the vessel, said occlusive member including an intrinsic resilient biasing force which biases the occlusive member to a contracted state for exerting an occluding pressure on the vessel while the occlusive member at least partially encircles the vessel; and a control mechanism operatively connected to said occlusive member for actuating the occlusive member to an expanded state, said control mechanism being arranged and configured to counteract the intrinsic resilient biasing force of said occlusive member and thereby force the occlusive member to the expanded state and remove the occluding pressure on the vessel while the occlusive member is at least partially encircling the vessel.

19. The apparatus according to claim 18, wherein said control mechanism comprises an actuating wire extending through the occlusive member and an actuator operatively connected to the actuating wire.

20. The apparatus according to claim 19, wherein one end of said actuating wire is fixed to said occlusive member, and said actuator is connected to an opposite end of said actuating wire and is capable of applying a pushing force to said actuating wire to force the occlusive member to the expanded state.

21. The apparatus according to claim 20, wherein said actuator comprises a housing and a plunger, said plunger and said housing being slideable relative to each other and said plunger being operatively connected to the opposite end of said actuating wire.

22. The apparatus according to claim 21, further comprising a mechanical advantage mechanism interconnected between the actuating wire and the plunger to amplify the movement of the plunger.

23. The apparatus according to claim 21, wherein said plunger has an activated position at which the occlusive member is in the contracted state and a deactivated position at which the occlusive member is in the expanded state, and said actuator further includes a locking mechanism for locking said plunger at the deactivated position.

24. The apparatus according to claim 18, wherein the occlusive member comprises an expandable and compressible polymeric material that is coated with an elastomeric material.

25. The apparatus according to claim 18, wherein said control mechanism includes a driver operatively connected to the occlusive member for forcing the occlusive member to the expanded state, and an abdominal pressure sensor adapted for sensing abdominal pressure, the driver being operable in response to the abdominal pressure sensed by the abdominal pressure sensor.

26. An apparatus comprising:

an expandable and contractable member adapted for at least partially encircling a body vessel, said member including an intrinsic resilient biasing force which biases the member to a contracted state;

an abdominal pressure sensor adapted for sensing abdominal pressure; and a control mechanism operatively connected to said member and interfacing with the abdominal pressure sensor, said control mechanism being arranged and configured to control expansion and contraction of the member in response to the abdominal pressure sensed by the abdominal pressure sensor.

27. A method for controlling fluid flow in a fluid conveying body vessel, comprising the steps of:

surrounding at least a portion of the vessel with a member that is resiliently biased to a contracted state such that an occluding pressure is exerted on the vessel when the member is in the contracted state; and selectively forcing the member to an expanded state thereby at least partially removing the occluding pressure on the vessel.

28. The method according to claim 27, wherein the step of surrounding includes surrounding a urethra for controlling fecal incontinence.

29. The method according to claim 27, wherein the step of surrounding includes surrounding veins of a penis for controlling venous outflow from the penis.

30. The method according to claim 27, wherein the step of surrounding includes surrounding a bile duct for controlling bile duct fluid flow.

31. The method according to claim 27, wherein the step of surrounding includes surrounding vas deferens for controlling fluid flow in the vas deferens thereby providing male fertility control.

32. The method according to claim 27, wherein the step of surrounding includes surrounding a fallopian tube for controlling fluid flow in the fallopian tube thereby providing female fertility control.

33. The method according to claim 27, wherein the step of surrounding includes surrounding a blood vessel for controlling fluid flow in the blood vessel.

34. The method according to claim 27, further including the step of sensing intra-abdominal pressure, and wherein the step of selectively forcing the member to an expanded state comprises forcing the member to the expanded state in response to the sensed intra-abdominal pressure.

* * * * *

UNITED STATES PATENT AND TRADEMARK OFFICE
CERTIFICATE OF CORRECTION

PATENT NO. : 6,074,341        Page 1 of 1
DATED : June 13, 2000
INVENTOR(S) : Anderson et al.

It is certified that error appears in the above-identified patent and that said Letters Patent is hereby corrected as shown below:

Title page,
Item [56], References Cited,
U.S PATENT DOCUMENTS, insert -- 3,749,098     7/1973     DeBennetot --; and insert -- 4,453,536     6/1984     Abild -- in appropriate order.

Signed and Sealed this

Twenty-fifth Day of December, 2001

Attest:

*Attesting Officer*

JAMES E. ROGAN
*Director of the United States Patent and Trademark Office*